June 10, 1969 H. A. JOHNSON, JR., ET AL Plant Pat. 2,891
STRAWBERRY PLANT
Filed July 10, 1967
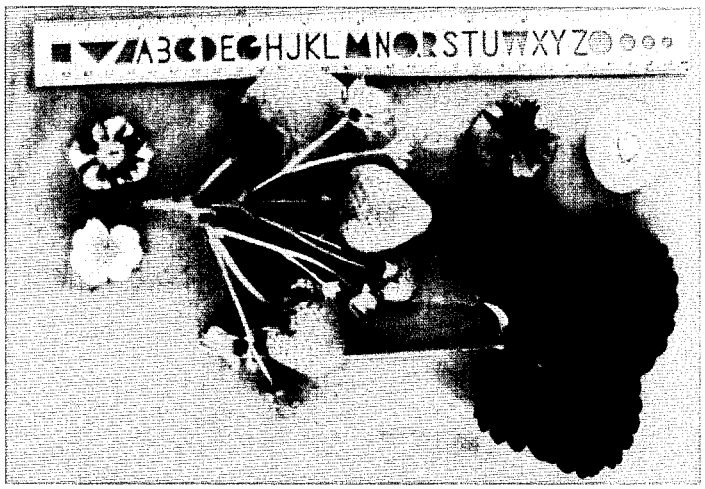
INVENTORS:
HAROLD A. JOHNSON, JR.
HAROLD E. THOMAS
BY
Townsend and Townsend
ATTORNEYS United States Patent Office Plant Pat. 2,891
Patented June 10, 1969

2,891
STRAWBERRY PLANT

Harold A. Johnson, Jr., and Harold E. Thomas, Morgan Hill, Calif., assignors to Driscoll Strawberry Associates, Morgan Hill, Calif., a corporation of California Filed July 10, 1967, Ser. No. 652,377
Int. Cl. A01h 5/08
U.S. Cl. Plt.—49 1 Claim This invention relates to a new and distinct variety of strawberry plant which is the result of a cross of the unpatented everbearing variety known as The Strawberry Institute of California selection No. E101.10 with the subject of United States Plant Patent No. 1,735 Goldsmith et al., issued July 29, 1958.

The seedlings resulting from the aforementioned cross were grown and asexually multiplied in Tehama County, Calif.; and tested in the fruiting beds of The Strawberry Institute's selection and testing grounds at San Martin, Calif. Clones of these seedlings were also held at The Strawberry Institute's Propagation Nursery in Shasta County. One plant was selected from the aforementioned group of seedlings, and further asexual reproduction was performed in the Shasta County nursery of the institute. Tests followed in various parts of California during intervening seasons on various institute members' properties. These tests indicated the merit of this new plant and resulted in its selection as a promising test variety.

A plant of the new variety typical in size, shape and color is pictured in the accompanying drawing in which three ripe berries are shown indicating some of the variations in shape found in this variety. To exemplify flesh color and core cavity a fourth berry is shown in cross section. The inflorescence pictured is typical of branching and relative size on and about the early part of June during which period the leaf is also typical in appearance and size. The flower, petals, and calyx shown are from secondary flowers.

This is a dark, compact, small to medium sized plant. It is an everbearing variety in that it may be planted during the spring as well as in December and a crop can still be realized the same growing year. This variety will crop until late fall, but it tends to crop in cycles, producing many large-sized berries at one picking. This large fruit size is characteristic of this variety and it will hold the good size as long as the plant remains vigorous. The plant is quite susceptible to the two-spotted mite, especially during the period of heavy cropping, and the mites often jeopardize the full value of this variety.

Other characteristics distinguishing this new variety are its fruit, cropping and plant characteristics. The berries have a high gloss with a generally smooth surface, with several ripening on a single inflorescence at once. The primary fruit has a distinct medium-conic to wedge shape and secondary and tertiary fruit become globose, and, in this regard, are different from the Goldsmith and the Institute E2 varieties. (The Institute E2 is an everbearing variety, United States Patent No. 2,611.) It is different in that its secondary and tertiaries are globose-wedge, becoming almost kidney shaped with the width greater than the length; this characteristic becomes even more pronounced as the picking season progresses. The secondaries and tertiaries of the Goldsmith and E2 do not become as globose or as wide in comparison to the length, as does this new variety.

The fruit of this new invention becomes darker in color sooner than does the Goldsmith or the E2. If the interval between picking becomes greater than three or four days in the Watsonville area, the surface color becomes darker than is acceptable by most fresh markets. The high gloss even when dark helps offset the consistent dark color of this variety. The flesh color is also darker and the core cavity smaller than the Goldsmith. The fruit size of this new variety may reach that of Goldsmith, but is generally not as consistently large. The fruit does not become malformed due to lack of pollen during cold, wet, windy periods as does Goldsmith. It does not generally produce longitudinal furrows or split at the apex as does the E2. The skin and flesh are equal to or slightly less firm than the Goldsmith.

This new variety has a distinct, large calyx which has more and deeper serrations at the apex of the sepals than the Goldsmith. The sepals also tend to overlap each other more often than does the Goldsmith. The inflorescence is similar to the Goldsmith in that many of the pedicels holding the primary berry originate from the axil formed by the union of peduncles. Many pedicels holding the primary berry may also originate from the side of one of the peduncles which is often the case with the Goldsmith. The inflorescence length is nearly equal that of the Goldsmith, but the new invention often ripens several fruit on one inflorescence at the same time.

A further characteristic of the new variety is that the plant is generally darker and smaller than Goldsmith, with petioles usually shorter, but leaflets are rugose to the same extent as Goldsmith but with serrations at the leaflet margin which are often double pointed, in contrast to the Goldsmith which normally has a single point at each serration.

If this new variety is planted during December, the time of crop production is similar to the Goldsmith, but if held for production until the second year, the new variety comes into production later than the Goldsmith. At the nursery, this new variety is considered a poor runner maker and produces fewer runner plants than the Goldsmith.

In comparision to the Goldsmith variety, many individuals consider the dessert quality of this variety superior, with a mild sub-acid flavor. There is generally no particular aroma peculiar to the flesh of this new variety.

This variety is susceptible to verticillium wilt, red stele, powdery mildew, and is very susceptible to the two-spotted mite. As a seedling this variety withstood the natural virus invasion of the virus components found in the Santa Clara Valley without losing its ability to produce.

The varietal characteristics of this new plant described below in detail were observed during the first fruiting season. Observations were made in the Salinas, Watsonville, and Pescadero areas of California which are cool coastal areas near the Pacific Ocean. The color terminology is in accordance with Ridgway's Color Standards and Nomenclature (1912 edition).

*Plant.*—Medium in size, open to slightly dense, with a medium root system.

*Leaves.*—Medium to large in size. The central leaflet diameter mostly 7 to 9 cm. in diameter, with the length usually equal to the width. Leaflets are moderately rugose, with serrations of the leaflet margins ovate with an acute apex, and often becoming double or triple pointed. Petioles are medium in length and bracts may be present. The leaflet upper side color at Watsonville in July is Dark Cress Green, Plate XXXI.

*Runners.*—Scarce, but vigorous when present. Nursery production is considered poor.

*Inflorescence.*—Medium in length, often producing several ripe berries on one inflorescence at one picking. The pedicel holding the primary berry may originate from a peduncle near the axil formed by the union of the peduncles, or it may originate from this axil (see drawing photograph). Most hair on the tertiary pedicel 20 mm. below the flower usually lays against and parallel to the pedicel but, at times, some hair forms an angle of 45 degrees with the pedicel. Flowers are visible above the foliage.

*Fruit.*—Large, dropping in size during the season. Primary berries during July average 40 to 45 mm. in length and 45 to 50 mm. in width. Primaries early in the picking season are mostly medium-wedge to medium-conic in shape as described in the U.S.D.A. Bulletin 1043, but as the season progresses the fruit becomes more globose. The shoulders of most berries are large and round, not necked. The fruit surface is smooth, firm, and dark in color with a high gloss. The surface color is Nopal Red, Plate I, to Carmine, Plate I. The flesh color is Strawberry Pink, Plate I, at the core, and Scarlet, Plate I, near the fruit perimeter.

*Seeds.*—Abundant and evenly spaced, medium in size, very few of which are non-fertile. The seeds are held mostly even with the fruit surface. The seed color is Apricot Yellow, Plate IV, becoming darker when exposed to full sunlight.

*Calyx.*—Large; the calyx of most primary berries is 40 to 45 mm. in diameter. Sepals are large and generally overlap each other, often becoming oblong or cuneate in form and deeply serrated at the apex. The calyx is usually free of the surface, but not often reflexed and is capped with difficulty when picking for processing. The sepal color on the side facing the fruit is Spinach Green, Plate V.

We claim:

1. The new and distinct variety of strawberry plant herein described and illustrated, and identified by the characteristics enumerated above.

No references cited.

ROBERT E. BAGWILL, *Primary Examiner.*